United States Patent [19]

Linkow

[11] Patent Number: 4,600,388
[45] Date of Patent: Jul. 15, 1986

[54] OSSEOUS INTEGRATED SUBMERGIBLE IMPLANT

[76] Inventor: Leonard I. Linkow, 1530 Palisade Ave., Fort Lee, N.J. 07024

[21] Appl. No.: 582,935

[22] Filed: Feb. 23, 1984

[51] Int. Cl.⁴ .................................................. A61C 8/00
[52] U.S. Cl. ....................................................... 433/176
[58] Field of Search ................ 433/173, 174, 175, 176

[56] References Cited

U.S. PATENT DOCUMENTS

| | | | |
|---|---|---|---|
| 3,589,011 | 6/1971 | Sneer | 433/174 |
| 3,919,772 | 11/1975 | Lenczycki | 433/173 |
| 3,952,414 | 4/1976 | Shovers et al. | 433/173 |
| 4,024,639 | 5/1977 | Weiss et al. | 433/173 |
| 4,044,467 | 8/1977 | Linkow et al. | 433/176 |
| 4,121,340 | 10/1978 | Patrick | 433/176 |
| 4,177,562 | 12/1979 | Miller et al. | 433/174 |
| 4,178,686 | 12/1979 | Riess et al. | 433/173 |
| 4,215,986 | 8/1980 | Riess | 433/173 |
| 4,522,596 | 6/1985 | Ashkinazy | 433/175 |

Primary Examiner—Robert Peshock
Attorney, Agent, or Firm—Darby & Darby

[57] ABSTRACT

Oral implants for original entry and re-entry procedures have implant portions that are positioned in grooves in the bone such that they are submergible below the upper rim of the bone. A post assembly for immediate installation of an artificial tooth structure may be detachably corrected to the implant portion. Alternatively, a cap may be attached and covered by tissue. Once the bone has grown over the implant portion, except in the area of the cap, the tissue is reopened and the cap is replaced by the post. In narrow bone areas the implant portion is a blade with a snap-on cap. In broad bone areas, the implant portion is box shaped and has a screw on post. If desired, the artificial tooth structure may be detachably connected to the post assembly for easy removal.

16 Claims, 13 Drawing Figures

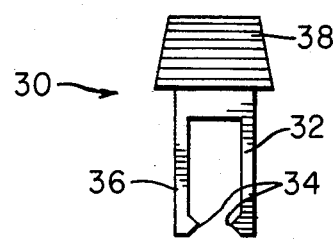
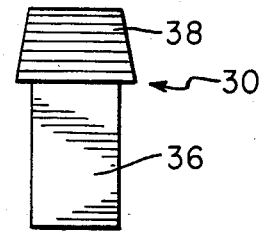
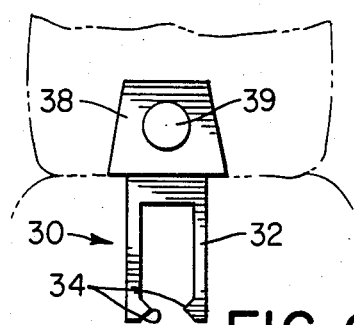
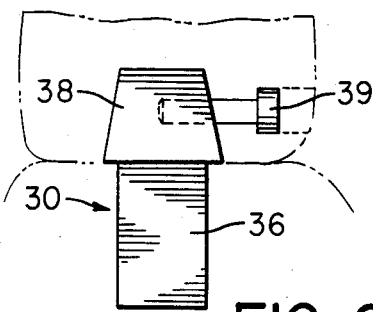
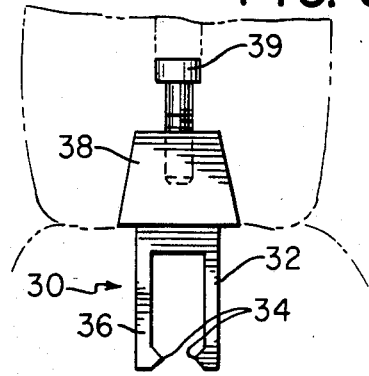
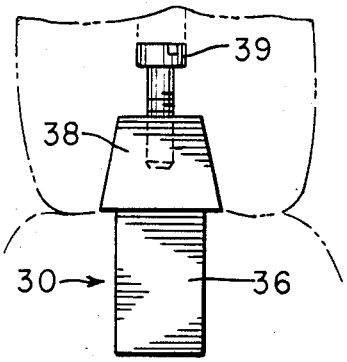
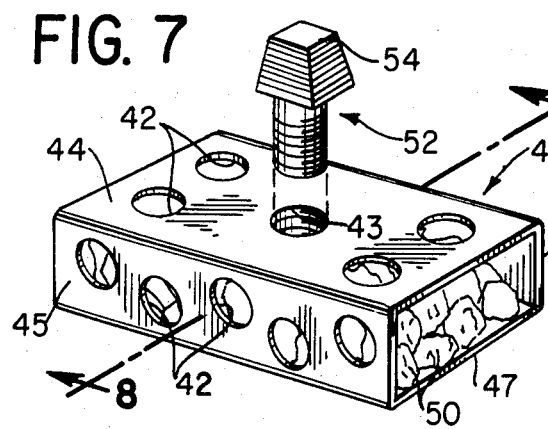
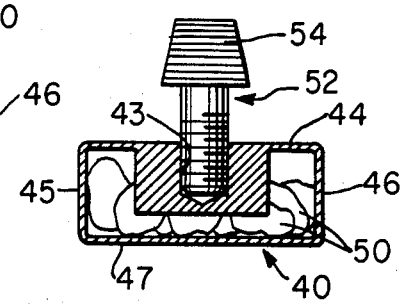

OSSEOUS INTEGRATED SUBMERGIBLE IMPLANT

BACKGROUND OF THE INVENTION

This invention relates to dental implants and, more particularly, to submergible implants.

A dental implant, such as that described in Pat. Nos. 3,465,441 and 3,660,899 of the present inventor are used to support an artificial bridge, tooth or other dental prosthesis. The implant has an implant portion, e.g. in the form of a blade, that is secured in the underlying bone in an edentulous span. A linking or neck portion, e.g. in the form of a screw, extends up from the implant portion and is attached to a support or post portion on which the artificial bridge or crown is attached. This type implant is inserted by making an incision in the fibromucosal tissue down to the underlying alveolar ridge crest bone. The tissue is then reflected to expose the bone and a burr is used to create a groove in the bone which is as deep as the implant portion. Using a mallet, the implant portion is tapped into the bone. After the insertion, the tissue is sutured about the neck portion so that the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

When a removable post is used, such as the screw shown in Pat. No. 3,660,899, the implant blade is made relatively broad, at least at the location of the post, in order to accommodate a threaded aperature into which the post is screwed. This threaded connection creates a substantial buccal-lingual width or bulge in the blade-type implants. Thus, when an implant is used in the narrow bone areas along the alveolar ridge crest of some patents, the remaining bone may be too narrow. This often leads to bone breakdown or "saucerization" of the resorbing bone in those areas.

Submergible blade implants, such as that shown in U.S. Pat. No. 4,177,562 of A. L. Miller and A. J. Viscido, allow a blade to be inserted in the jawbone for a long period of time before being placed in actual use. With this type of implant the blade is completely submerged in the bone. It is then covered over and allowed to remain in place for several months. Once there has been substantial regrowth of the bone around and through the submerged blade, the tissue is again opened and the post is attached to the blade by the typical screw connection. Because of this screw connection, this submergible blade also has a rather wide buccal-lingual dimension. Further, this design employs additional screws that act to spread the blade. Consequently, this implant may not be suitable for use in narrow bone areas.

Bone areas where either a group of teeth or an implant had to be removed because of loosening, often leave a great deal of bone destruction in the original site. To install an implant in the enlarged area left behind, it is necessary to use a basket or tubular type implant portion such as those disclosed in U.S. patent application Ser. No. 516,184 of the present inventor, which application was filed July 21, 1983 and is entitled "Oral Implant For Oversized Dental Support Openings". Since the bone in the area has already been significantly damaged, it may be desirable to allow a considerable waiting period before the dental prosthesis is applied to the post portion of this implant and it is put into use. However, significant loosening of this implant may occur simply due to contact between the patient's tongue and the neck or post of the implant. Further, the implants in this patent application which are provided with screw type posts, have a generally rounded cross section and may shift in position due to contact with the tongue.

Removable posts are necessary with submergible implants which are to remain out of use for a period of time while the bone regrows. These screw posts are also useful with non-submergible implants because they allow the blade to remain in place when a defective bridge is removed. However, the bridge is usually destroyed when it is removed. In some cases, it is the blade which is defective; but, currently the perfectly good bridge, which is permanently cemented over the posts, must still be destroyed in order to replace the defective implant.

SUMMARY OF THE INVENTION

The present invention is directed to providing a submergible implant (a) of narrow continuous cross section suitable for insertion in the narrow alveolar crest ridge of some patients or (b) of broad cross section suitable for immediate re-entry procedures in openings in the underlying bone caused by the removal of over-retained teeth or a prior failed implant. With both submersible implant types, the posts are detachably connected to the implant portion.

In an illustrative embodiment of the invention, the oral implant includes an implant portion, e.g. a blade, adapted to be fitted in an opening prepared in the jawbone such that it is submerged below the upper rim of the opening. This implant portion has at least one location along its length where the post for supporting an artificial crown or bridge can be attached to it. However, during the initial procedure, a plastic protective cap with depending legs is positioned at the connection location and the surrounding tissue is closed over the implant. After a few months bone grows over the implant portion and through vent holes provided in it, but the cap prevents bone growth at the connection location. In a subsequent procedure after the implant portion is firmly anchored due to bone regrowth, an incision is made in the gum tissue. The plastic cup is removed and a post assembly (including legs, a neck portion and a post portion) is connected to the implant portion. As a result, no forces are applied to the implant portion by the patient's tongue or teeth prior to the firm anchoring of it.

Preferably, the connection of the cap or post to the implant portion is established by projections from the legs on the cap or post which snap fit into recesses in the implant portion at the connection locations where the legs of the cap or post straddle it. Because the post is snap fit over the implant portion, there is no need for buccal-lingual bulges in the implant portion to accommodate a threaded hole to receive a threaded post, as in the prior art. Consequently, the implant portion can be made in the form of a thin blade which can be used in narrow bone. However, screw connections can be provided between the prosthesis and the post assembly to permit the prosthesis to be removed without destroying it, while still leaving the snap-on post assemblies attached to the blade. Also the snap-on post assemblies and the bridge can be tapped off the buried blade together in one piece without affecting the blade.

In relatively wide bone areas that have enlarged openings, a box type submergible implant portion is used. If the walls of the enlarged opening are made parallel and the box is wedged between these walls, it cannot rotate about its axis as is possible with the tubular implants disclosed in the applicant's prior patent application. In addition, the box shape, unlike the blade shape shown in the previously identified Miller, et al. patent, is wide enough to be wedged in the enlarged opening without waiting for bone regrowth and the interior portion of the implant portion can be filled with bone fragments which will promote the rapid regrowth of bone to anchor the submergible implant portion.

The posts for the box type implant can be attached to the implant portion by conventional screw threads or snap-fit connections and immediately placed into function. Alternatively, a cap can be placed over the connection and the incision sutured. After bone regrows the tissue is reopened and the cap is replaced with a post so as to put the implant into function.

BRIEF DESCRIPTION OF THE DRAWINGS

The foregoing and other features of the present invention will be more readily apparent from the following detailed description and drawings of illustrative embodiments of the invention in which:

FIGS. 4A and 4B are end and side views, respectively, of the post assembly of FIG. 1;

FIGS. 5A and 5B are end and side views, respectively, of a post assembly for an implant wherein the post is attached thereto by a horizontal screw;

FIGS. 6A and 6B are end and side views, respectively, of a post assembly for an implant wherein the post is attached thereto by a vertical screw;

FIG. 7 is an exploded perspective view of a box-type submergible implant according to the present invention; and FIG. 8 is a cross-sectional view along line 8—8 of the implant of FIG. 5.

DESCRIPTION OF ILLUSTRATIVE EMBODIMENTS

Figure 1:
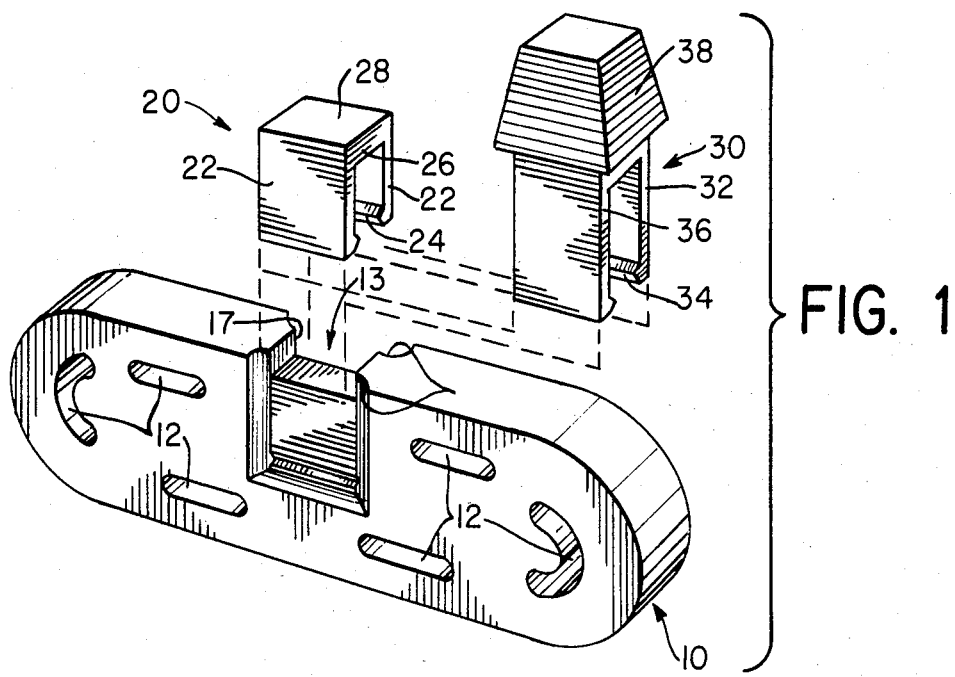
FIG. 1 is an enlarged exploded perspective view of a narrow submergible implant according to the present invention.

In FIG. 1 there is shown a greatly enlarged embodiment of the invention suitable for use in the narrow alveolar ridge crest of some patients. This implant includes a implant portion 10 in the form of a blade which may be made from titanium, vitalium, surgical stainless steel or other typical implant material. This blade has holes or vents 12 through it which allow bone to grow completely through the blade so as to anchor the implant in place.

Figure 2A:
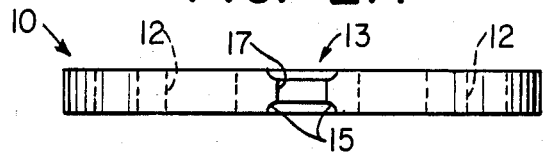
FIG. 2A is a top view of the implant portion of the implant of FIG. 1

As best shown in FIG. 2, the blade is relatively narrow and has no buccal-lingual bulges to accommodate a threaded aperture. Instead, it is narrowed at a connection position 13 by means of indentations 15. In addition, the blade has a vertical cutout 17, typically of 1 to 2 mm, at the connection position 13, as shown FIG. 1. Position 13 is adapted to receive a cap 20 or a post assembly 30. The cap 20 is designed to straddle the recessed portion of the blade with its downwardly extending legs 22. At the ends of these legs inward projections 24 may be provided as shown in greater detail in FIG. 3A. These projections 24 engage in recesses 14 located in the blade below the vertical cutout 17 at connection position 13. However, simple frictional contact between the legs and the blade may be sufficient to connect the cap to the post. The body portion 26 of cap 20 is designed to have a height that will make its upper surface 28 generally flush with the top surface 16 of the blade when the cap is positioned on the blade.

By making the cap of Teflon, or another flexible material, including flexible metals, the cap can be positioned to straddle the blade and then pushed down so that the projections 24 snap fit into recesses 14. In this position, the body portion 26 of the cap fills the slight vertical cutout 17 so the top of the cap is generally flush with the top of the blade. Also, in the installed position the legs of the cap fit into the the horizontal indentations 15 in the blade shown in FIG. 2 so that they generally do not extend beyond the width of the blade and the overal surface is flush on the buccal and lingual sides of the blade in the recessed areas.

In practicing the invention, the implant of FIG. 1 is selected by the dentist or oral surgeon when the patient has a narrow alveolar ridge crest, such as a knife edge ridge or a shallow ridge, where the use of a conventional blade or other type of implant is contraindicated because of possible destruction of the narrow bone by the insertion of such a conventional implant and the placing of it into immediate function. The implant of FIG. 1 is also useful when no bone exists, e.g. where there is a completely resorbed upper crest. In such a case, the surgeon can implant the blade of FIG. 1 by bisecting the palatal cortex on the palatal side. Because of the narrow shape of the blade the maxillary sinus will be avoided.

The blade implant of FIG. 1 is installed in a conventional manner. In particular, an incision is made in the fibromucosal tissue down to the underlying bone in the edentulous span. The tissue is reflected and a groove is drilled in the bone using a burr. This groove is made about the width of the blade so that it can be snuggly fit therein, perhaps with the aid of gentle tapping with a mallet. The groove is also made deep enough for the blade to be submerged in the groove below its upper rim. Once the blade is in place, the cap is snapped onto the blade. This can be done without pressure on the side walls of the groove because of the indentations 15 in the blade. The tissue is next sutured over the blade and cap. As a result, no part of the cap protrudes above the tissue and consequently the blade remains out of function, and protected from impact with the patient's tongue and other teeth.

A few months are allowed to pass during which the surrounding bone becomes integrated with the blade, i.e. grows into direct contact with the bone without the presence of the intervening tissue normally found with immediately functioning blades. The bone also grows through the vents 12 in the blade and over its upper surface 16. However, the cap prevents bone growth in the connection area 13.

Once the dentist or surgeon is sure that the blade is firmly anchored in the bone, a new incision is made in the tissue and the cap is removed. In place of the cap, the post assembly 30 is snap-fit onto the blade. This post assembly can be made in one piece of titanium, vitalium, surgical stainless steels (such as 304 or 316L) or it can be made of softer material such as Teflon or some other plastic material.

The lower portion of the post assembly duplicates the shape of the cap. In particular, it has two downwardly depending legs 32 that straddle the blade at the connection 13. These legs may have inward projections 34 that snap into the recesses 14 in the blade or there may merely be a friction connection between the legs and the blade. A neck portion 36 of the post extends upwardly above the top surface 16 of the blade and terminates in a post portion 38 upon which the artificial crown or bridge is to be fastened. The design of the post assembly is shown in more detail in FIGS. 4A and 4B.

As with the cap, the cross section of each leg 32 of the post longitudinal assembly fits within an indentation 15 of the blade and the flat portions of the legs fit flush with the buccal and lingual surfaces of the blade so there are no buccal-lingual bulges. However, as an alternative to the design shown in FIG. 4, the upper neck portion 36 of the post assembly above the bone line can be made wider buccal lingually than the blade without causing difficulty.

Regardless of the design of the post assembly selected, it can be made so that it is rigidly supported on the blade or it can be made to have a slight amount of play, back and forth and side to side. This play may be, for example, 0.1 to 1 mm. This is equivalent to the normal play in a tooth root which is due to the surrounding periodontal membrane. Therefore with the blade being nearly or totally osseously integrated, a slightly movable post assembly causes only a very little force to be brought to bear on the blade portion itself. Instead, the neck portion of the post assembly acts as a stress distributing member.

Figure 2B:
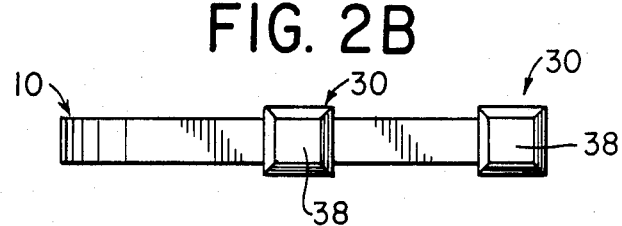
FIG. 2B is on top view of an alternative implant portion with two post attached.
Figure 3A:
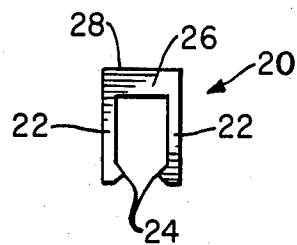
FIGS. 3A and 3B are end and side views, respectively, of the straddling cap of FIG. 1.
Figure 3B:
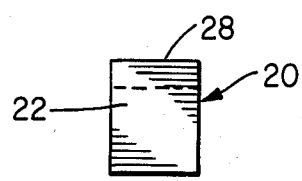

While FIG. 1 shows one post assembly 30 mounted on blade 10, it is possible to design the blade to accept more than one such post assembly. In such a case, several connection positions would be located along the length of the blade at positions where posts are desired. FIG. 2B shows a top view of an arrangement with two posts mounted to a single blade.

A bridge may be fastened to the post portion 38 of the post assembly 30 by cement or another adhesive. Thus, it is permanently attached to the implant post. However, if the blade should come loose for some reason, it was previously necessary to destroy the perfectly good bridge in order to remove the failed blade. This is avoided with the present invention. In particular, all that is necessary is to open the tissue and unsnap the post assembly from the blade. A new blade may then be installed and the previous post assembly and bridge combination may be snapped onto the new blade. It is also possible to attach the crown or the bridge and the attached post portion to the rest of the snap-on post assembly by either horizontal or vertical screws 39 that go through the post into the neck portion as shown in FIGS. 5 and 6. If a small hole is left in the artificial crown or bridge at the location of the post, the bridge and attached post can be removed from the implant by loosing these screws without removing the rest of the snap-on post assembly.

If the implant fails because the blade becomes loose before bone regeneration occurs, prolonged retention of the blade will allow it to enlarge the groove in the bone. The same thing can happen when periodontally-involved teeth are over retained. When the groove or tooth socket has become oversized, e.g. up to ¼ inch in width or more, the initial submergible implant of FIG. 1 is not effective for immediate use. Instead the dentist must wait for bone to grow and fill the opening and then he must form a new groove in the new bone. However, as an alternate, the dentist may use an immediate re-entry type implant, such as the horizontal submergible box type shown in FIGS. 7 and 8.

The implant of FIG. 7 uses an implant portion 40 with a hollow rectangular or square cross section (FIG. 8). This portion has vents 42 in it to promote bone growth. Also, the interior may be filled with natural or artificial bone fragments 50 to aid in the formation of a solidified mass of bone in the enlarged opening.

The box implant portion can have one or more threaded apertures 43 in its upper surface 44. Here, the width of the box implant portion, which is great enough to permit the use of threaded apertures, is not a problem because of the size of the existing groove. In fact, the implant portion is designed to be wide enough for its lateral side walls 45, 46 to be wedged against the remaining buccal and lingual cortices of the bone of the groove after the oversized and resorbed original groove has been fashioned with a fissure type burr to be parallel. During the fashioning of the groove, its bottom is also made flat so as to correspond to the bottom side 47 of the implant portion. As a result this re-entry type implant can be tapped into position with a mallet and will immediately remain rigidly in place. It is also positioned deep enough in the groove so that its top surface 48 is at least 3 mm below the height of both the buccal and lingual cortices. This allows the bone to grow completely over its upper surface, as well as completely internally through its vents and through its entire hollow cross section.

Either immediately or after waiting 3 to 6 months, a threaded post assembly 52, having a post portion 54 at its upper end, is screwed into an aperture 43. If the surgeon elects to wait before putting the implant into operation, a Teflon plug is placed in the aperture to prevent bone from filling it. Alternatively, the post assembly can be screwed into place immediately. The implant portion 40 will not rotate because its parallel walls are against the parallel walls of the groove. Thus, it will be stable from the first day of use.

The rectangular tubular implant portion can be made in sections as long as one foot or more. Such a long section can then be cut down to size, as and when needed. Also, the sections can be made in different sizes, with the one closest in size to the re-entry groove being selected for use. Further, the box implant portion can be made of a deformable metal that will allow it to be shaped to assure a tight fit in the groove.

While the invention has been particularly shown and described with reference to preferred embodiments thereof, it will be understood by those skilled in the art that various changes in form and details may be made therein without departing from the spirit and scope of the invention.

I claim:
1. An oral implant for supporting an artificial tooth structure, comprising:
   an implant portion having opposite side walls and being adapted to be fitted in an opening in a bone in the vicinity of the occlusal plane, which bone has been exposed by an incision in the covering fibromucosal tissue, said implant portion being adapted to be submerged below the upper edge of the opening in the bone; and at least one post assembly having a neck portion and a post portion, the neck portion of said post assembly being detachably connected to said implant portion and being adapted to straddle said implant and to make friction contact with its opposite side walls when connected thereto, the post portion being adapted to receive the artificial tooth structure.

2. An oral implant as claimed in claim 1 wherein the post is made from one of the materials titanium, vitalium or surgical stainless steel.

3. An oral implant as claimed in claim 1 wherein the artificial tooth structure is a bridge.

4. An oral implant as claimed in claim 1 wherein said implant portion is in the form of a blade having a length and width, the width of the blade with the post mounted thereon being relatively narrow and constant over its length.

5. An oral implant as claimed in claim 4 wherein the neck portion has depending legs that straddle said blade, said legs having projections at their ends that snap into at least one pair of recesses in opposite side walls of the blade.

6. An oral implant as claimed in claim 5
wherein the blade has at least one pair of lateral indentations spaced along its length at a connection position, the pair of recesses being at the connection position and the recesses of the pair being on the opposite side walls of the blade, and
wherein the projections of the leg portions snap into the recesses when the post assembly is installed on the blade at the connection position, and the legs fit within the indentations of the blade so that their outer surfaces are relatively flush with the lateral surfaces of the blade.

7. An oral implant as claimed in claim 6 including a plurality of integral post assemblies and pairs of recesses, each post assembly being snap fit to a separate pair of said plurality of pairs of recesses.

8. An oral implant as claimed in claim 1 wherein said implant portion is a hollow box having a length and width, the width being relatively constant over its length and the width being great enough to cause it to be wedged in an opening in the bone caused by the removal of overly-retained loose teeth or a previously inserted failed implant.

9. An oral implant as claimed in claim 1 wherein the implant portion has an upper surface and further including a cap adapted to straddle the implant portion, said implant portion having a vertical cutout in its upper surface and the cap being designed to be seated in the cutout such that said cap does not extend significantly above the upper surface of the implant portion.

10. An oral implant as claimed in claim 9 wherein the legs of the cap have projections at their ends that snap fit into recesses in the blade when the cap straddles the blade at a connection position.

11. An oral implant as claimed in claim 1 wherein the artificial tooth structure and post portion are detachably connected to the neck portion.

12. An oral implant as claimed in claim 11 wherein the artificial tooth structure and post portion are connected to the neck portion by screws.

13. An oral osseous implant for supporting an artificial tooth structure, comprising:
an implant portion having opposite side walls and being adapted to be fitted in an opening in a bone portion in the vicinity of the occlusal plane which has been exposed by an incision in fibromucosal tissue covering it, said implant portion being adapted so that it is submerged below the upper rim of the opening and having an upper surface facing away from the opening when installed therein, and
a cap detachably connected to said implant portion, said cap having a body and downwardly depending legs adapted to straddle the implant portion and to make friction contact with its opposite side walls when connected thereto, the cap further being adapted so that it does not extend significantly above the upper surface of the implant portion and can be covered by fibromucosal tissue when the implant is installed.

14. An oral implant as claimed in claim 13
wherein the implant portion is a relatively narrow blade with an upper surface and at least one pair of lateral indentations located adjacent at least one connection position, the blade also includes a shallow vertical cutout at the connection position and a pair of recesses below the cutout, one recess of the pair being on each side wall of the blade, and
wherein the cap legs have projections that snap into the recesses when straddling the blade, the legs being received in the indentations so they do not extend beyond the lateral width of the blade, and the cap body resting in the cutout so its surface remote from the legs does not extend significantly above the upper surface of the blade when installed thereon, said cap preventing regrowth of bone in the area of the blade where the cap is located.

15. An oral implant as claimed in claim 13 wherein the cap is made of plastic material.

16. An oral implant as claimed in claim 13 wherein the cap is made of Teflon.

* * * * *